(12) United States Patent
Nearpass

(10) Patent No.: US 6,832,750 B2
(45) Date of Patent: Dec. 21, 2004

(54) BACK SEATING VALVE WITH SERVICE PORT

(75) Inventor: Gary A. Nearpass, Clyde, NY (US)

(73) Assignee: Parker-Hannifin Corporation, Cleveland, OH (US)

( * ) Notice: Subject to any disclaimer, the term of this patent is extended or adjusted under 35 U.S.C. 154(b) by 89 days.

(21) Appl. No.: 10/197,884

(22) Filed: Jul. 17, 2002

(65) Prior Publication Data

US 2003/0020041 A1 Jan. 30, 2003

Related U.S. Application Data

(60) Provisional application No. 60/307,782, filed on Jul. 25, 2001.

(51) Int. Cl.$^7$ .............................................. F16K 41/18
(52) U.S. Cl. ..................... 251/330; 251/365; 137/625.5
(58) Field of Search ................................ 251/330, 365; 137/15.21, 15.18, 315.09, 315.28, 625.48, 625.49, 625.5, 866, 614.18, 614.13; 29/890.13; 285/256

(56) References Cited

U.S. PATENT DOCUMENTS

| | | | |
|---|---|---|---|
| 188,556 A | * 3/1877 | Wiggins | 137/625.5 |
| 261,224 A | * 7/1882 | Groshon | 137/625.5 |
| 1,490,884 A | * 4/1924 | Spreen | 251/330 |
| 1,502,734 A | 7/1924 | Martin | |
| 1,972,821 A | * 9/1934 | Weatherhead, Jr. | 137/625.5 |
| 2,209,709 A | * 7/1940 | Weatherhead, Jr. | 137/625.5 |
| 2,682,386 A | * 6/1954 | Lindsay | 137/625.5 |
| 2,924,232 A | 2/1960 | Michaels | |
| 2,964,290 A | 12/1960 | Mueller | |
| 3,198,211 A | * 8/1965 | Gray, Jr. | 137/625.48 |
| 3,382,894 A | * 5/1968 | Shurtleff et al. | 137/625.5 |
| 3,593,745 A | * 7/1971 | Myers | 137/625.5 |
| 3,623,699 A | 11/1971 | Matousek | |
| 3,762,443 A | 10/1973 | Sorenson | |
| 3,777,783 A | 12/1973 | Beck | |
| 3,789,881 A | 2/1974 | Kozulla et al. | |
| 3,851,853 A | 12/1974 | Teeters | |
| 4,215,714 A | * 8/1980 | Laue | 137/625.5 |
| 4,364,543 A | 12/1982 | Soya et al. | |
| 4,521,948 A | 6/1985 | Lane | |
| 5,067,521 A | 11/1991 | Jenks et al. | |
| 5,120,020 A | 6/1992 | Lane | |
| 5,797,629 A | * 8/1998 | Beagle | 285/256 |

FOREIGN PATENT DOCUMENTS

DE        19618272 A1    11/1997

OTHER PUBLICATIONS

Copy of Notification of Transmittal of the International Search Report or the Declaration from corresponding PCT Application No. PCT/US02/23023.

\* cited by examiner

*Primary Examiner*—Eric Keasel
(74) *Attorney, Agent, or Firm*—Christopher H. Hunter

(57) ABSTRACT

A back seating valve includes a valve body enclosing a valve plug with a threaded through-bore; and a valve element with a threaded valve stem and valve head. The valve plug and valve stem are initially preassembled, and then inserted into the valve body. The valve body is mechanically formed to retain the valve plug in the valve body without the use of welding or brazing. The valve plug has an external, non-cylindrical geometry which prevents the valve plug from rotating within the valve body. The valve plug is axially held between a shoulder and a narrowed-down end in the valve body. An external portion of the valve stem can be rotated to move the valve head into open, intermediate and closed positions between a front valve seat in the valve body, and a back valve seat in the valve plug.

43 Claims, 4 Drawing Sheets

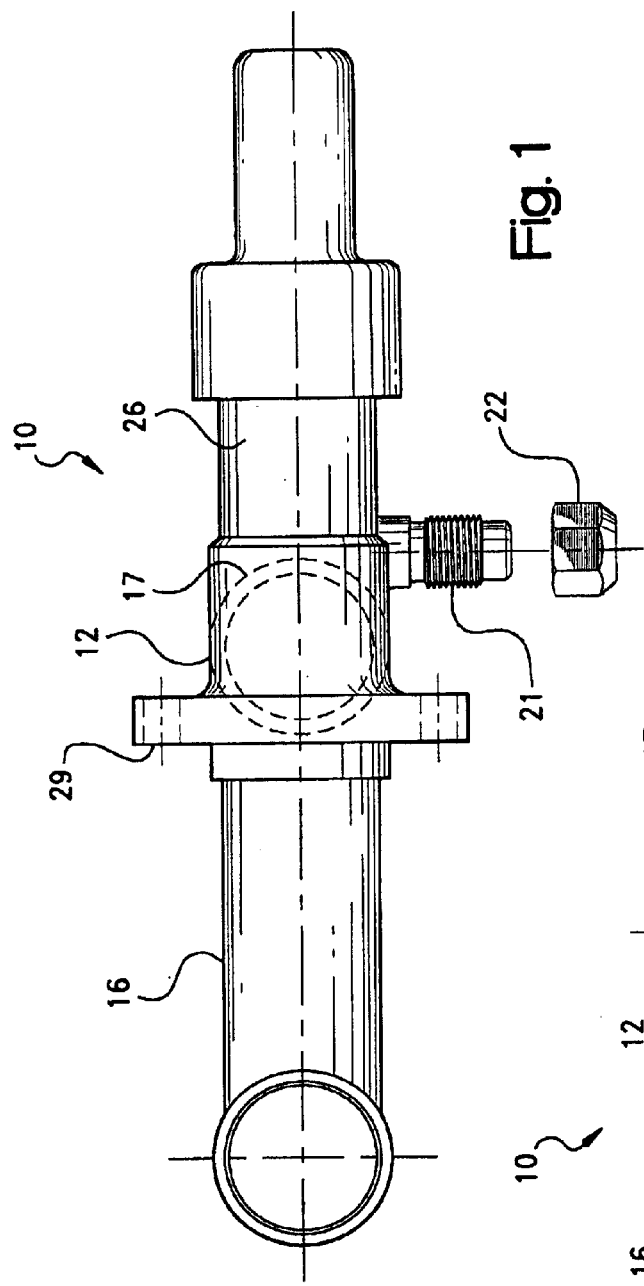
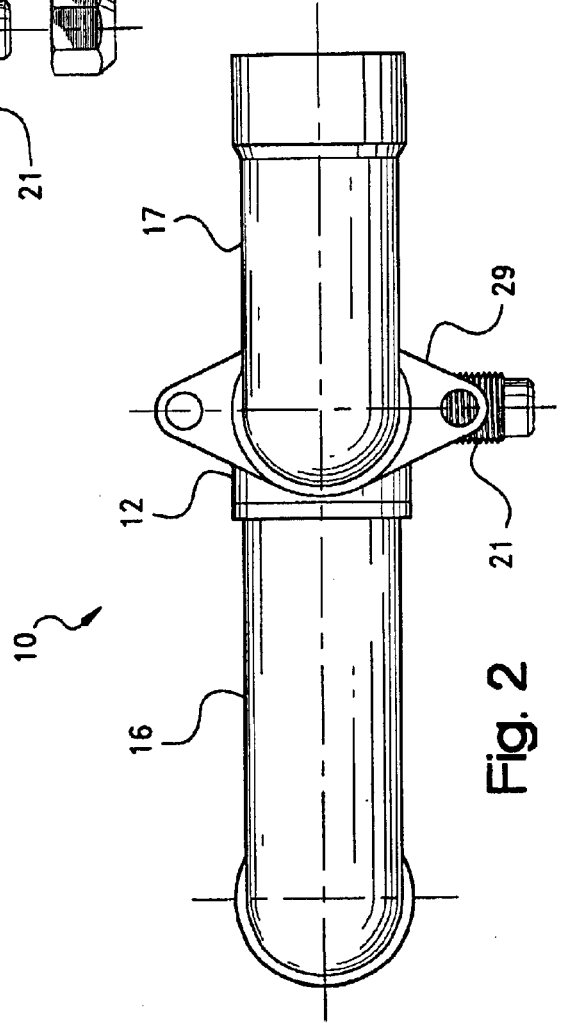

BACK SEATING VALVE WITH SERVICE PORT

CROSS-REFERENCE TO RELATED CASES

The present application claims the benefit of the filing date of U.S. Provisional Application Ser. No. 60/307,782; filed Jul. 25, 2001, the disclosure of which is expressly incorporated herein by reference,

BACKGROUND OF THE INVENTION

The present invention relates to valves which have a service port to enable evaluation of fluid in a fluid system.

Back seating valves with service ports are known, and are used in a variety of applications, for example in refrigeration systems. The valve is located in a fluid system and includes first, second and third fluid passages. The first and second passages comprise the inlet and outlet passage for the valve, while the third passage comprises a service port. A valve element can be moved between open, intermediate and closed positions in the valve to i) allow fluid to pass from the inlet passage to the outlet passage in the valve substantially uninterrupted during normal system operation (open position); ii) open a flow path to the service port for evacuation, charging, reclaiming and pressure-tapping the system (intermediate position); or iii) completely close the flow path between the first and second passages during shipping and maintenance (closed position). The valve element is typically externally accessible to allow manual manipulation of the valve into the respective positions, although the valve could also be operated automatically using electromechanical devices (e.g., solenoids, etc.).

It is believed that many of the commercially-available back seating valves include a valve element and a valve seat which are separately assembled into the valve body, sometimes from opposite ends of the body. The valve seat may be first inserted through the service port opening and welded, brazed or threaded into the valve body, and the valve element is then inserted through the inlet passage or outlet passage opening before the inlet passage tube/fitting or outlet passage tube/fitting is attached to the valve body. The brazing/welding/threading of the valve seat, however, adds a potential leak path through the system; while the brazing/welding process requires more expensive valve seats to be used that can withstand the higher temperatures associated with the brazing/welding process.

It is also believed that many of the available valves include numerous components which can require complicated and/or time-consuming assembly steps, and which thereby add to the manufacturing, assembly and maintenance/repair costs of the valve, and increase the potential leak paths through the valve. This can all contribute to a higher operating cost for the fluid system. The additional component parts can also increase the over-all size and weight of the valve.

Some of the back seating valves also allow an operator to remove the valve element while the valve is connected within the fluid system. While the field-repair of a valve may be appropriate in some circumstances, it can also lead to accidental removal of a valve element while the fluid system is operating, thereby allowing fluid to spill from the valve or the valve to be disabled; and can allow incompatible or inappropriate replacement valve elements to be used with the back-seating valve.

It is thereby believed there is a demand for an improved back-seating valve with service port which i) has fewer brazing and/or welding steps and fewer components to reduce manufacturing and assembly costs, and to reduce leak paths; and ii) prevents disassembly of the valve in the field.

SUMMARY OF THE INVENTION

The present invention provides a novel and unique back seating valve with a service port. The back seating valve of the present invention has few braze/welding joints and few components, which reduces manufacturing and assembly costs and reduces leak paths; and the valve cannot be disassembled in the field.

According to the present invention, the back seating valve includes a valve plug having a central threaded through-bore; and a valve element with an elongated stem and an integral valve head. The stem has a threaded portion which is screwed into the through-bore in the valve plug. The valve plug and valve stem are initially preassembled, and then inserted into the valve body. The valve body is then mechanically formed (e.g., crimped, coined or magnetically formed) to retain the valve plug in the valve body without the use of welding or brazing. The valve plug has an external, non-cylindrical geometry, which, after the valve body is crimped and adopts the non-cylindrical geometry of the valve plug, prevents the valve plug from rotating within the valve body. The valve body also has an internal shoulder which supports one end of the valve plug, and is mechanically narrowed at its opposite open end to support the other end of the valve plug, thereby also preventing axial movement of the valve plug in the valve body.

The valve plug has a first valve seat (back valve seat) at its upstream end, and the valve element can be rotated to bring the valve head into sealing engagement with the first valve seat. An enlarged counterbore extends inwardly into the valve plug from the valve seat, and a plurality of radial passages fluidly interconnect the counterbore with an annular channel outwardly surrounding the valve plug. The channel is in axial alignment with a service port in the valve body to provide a flow path through the valve plug. A second valve seat (front valve seat), for the inlet passage, is also provided axially opposite from the back valve seat for the valve plug.

The stem of the valve element has a portion which extends externally from the downstream end of the valve plug, and is externally accessible to rotate the valve element, and bring the valve head into and out of sealing engagement with the valve seats.

The valve element can be moved into an open position for normal system operation where the valve head is in sealing engagement with the back valve seat and fluid can flow substantially uninterrupted (without significant pressure drop) from the inlet passage to the outlet passage. The valve element can also be moved into a closed position, where the valve head is in sealing engagement with the front valve seat, to prevent fluid flow through the valve during maintenance and shipping. The valve element can also be moved into an intermediate position, where the valve head is spaced from both the front and back valve seats, such that a flow path is opened to the service passage for evacuating, charging, reclaiming and pressure-tapping the system. A stem cap fits over the end of the valve body to enclose the external portion of the stem when the valve element is not being moved.

The valve plug and valve element can be formed of inexpensive material, such as elastomers and plastics, as the plug is not subject to brazing or welding temperatures during assembly. This can also reduce the weight of the valve. The valve element and valve plug can also be pre-tested prior to being inserted into the valve body, to ensure the valve is in compliance with operating specifications. The pre-assembled valve plug and valve element can be easily inserted into the valve body from one end of the body, and after the valve body is mechanically deformed, cannot be removed from the valve body.

Appropriate seals can be provided between the valve stem and the valve plug and/or between the valve plug and the valve body to prevent fluid leaking from the valve.

Thus, it should be appreciated that the back seating valve of the present invention has few braze/welding joints and few components, which reduces manufacturing and assembly costs, and reduces leak paths; and cannot be disassembled in the field.

Further features of the present invention will become apparent to those skilled in the art upon reviewing the following specification and attached drawings.

BRIEF DESCRIPTION OF THE DRAWINGS

FIG. 1 is a top view of a back-seating valve constructed according to the principles of the present invention;

FIG. 2 is a bottom view of the valve of FIG. 1;

DETAILED DESCRIPTION OF THE PREFERRED EMBODIMENT

Figure 3:
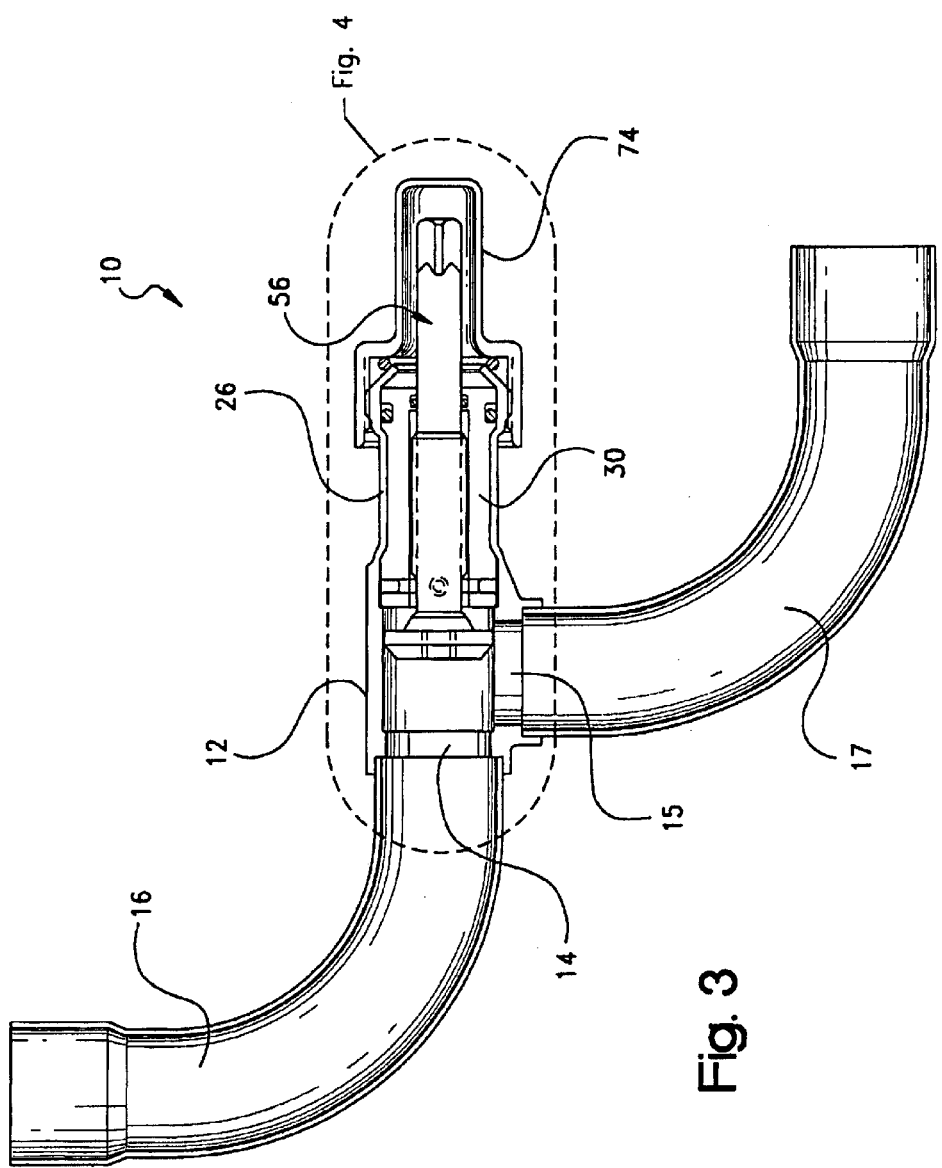
FIG. 3 is a cross-sectional side view of the valve.

Referring to the drawings, and initially to FIGS. 1–3, a valve constructed according to the principles of the present invention is indicated generally at 10. Valve 10 is a back-seating valve as will be described more fully below, and includes a valve body 12 with first and second ports or passages 14, 15. First and second copper tubes 16, 17, are fixed (e.g., brazed, welded, etc.) to first and second ports 14, 15, respectively. First and second tubes 16, 17 can be fluidly connected in an appropriate manner (e.g., brazed or welded) within a fluid system, such as a refrigeration system, as should be appreciated by those of ordinary skill in the art. Typically, first tube 16 is an inlet tube directing fluid in the system to first port 14, which is considered an inlet port; and second port 15 functions as an outlet port directing fluid to a second tube 17, which is considered an outlet tube—but it should be appreciated that the valve could be connected in a reverse manner, or the fluid system could operate in reverse, so that the terms "inlet" and "outlet" should be considered interchangeable.

Figure 5:
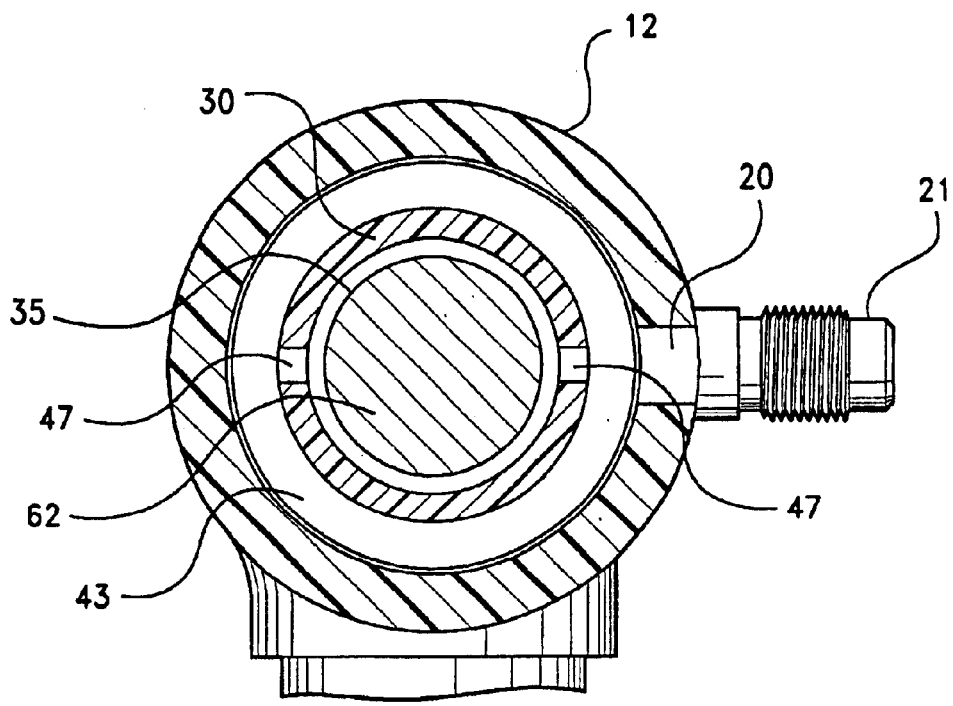
FIG. 5 is a cross-sectional end view of the valve taken substantially along the plane designated by the lines 5—5 in FIG. 4.

Valve body 12 further includes a third, or service port 20 (FIG. 5), which is located downstream of inlet port 14. Service port 20 includes a short copper fitting or forged fitting 21 which is also fixed (e.g., brazed, welded, forged, etc.) to valve body 12, and externally threaded to facilitate attachment of external tubing. Fitting 21 is protected by a cap 22 (FIG. 1), when the service port is not being used. The first, second and third ports 14, 15, 20 open into a valve chamber 24 located centrally in the valve body. Port 14 defines a circular, front or second valve seat 25 in the valve body 12. It should be noted that first port 14 intersects one end of valve body 12, and both second and third ports 15 and 20 intersect the body essentially perpendicular to the first port, but this is merely for illustration purposes, and second and third ports 15 and 20 could intersect the valve body at other than perpendicular angles.

Figure 4:
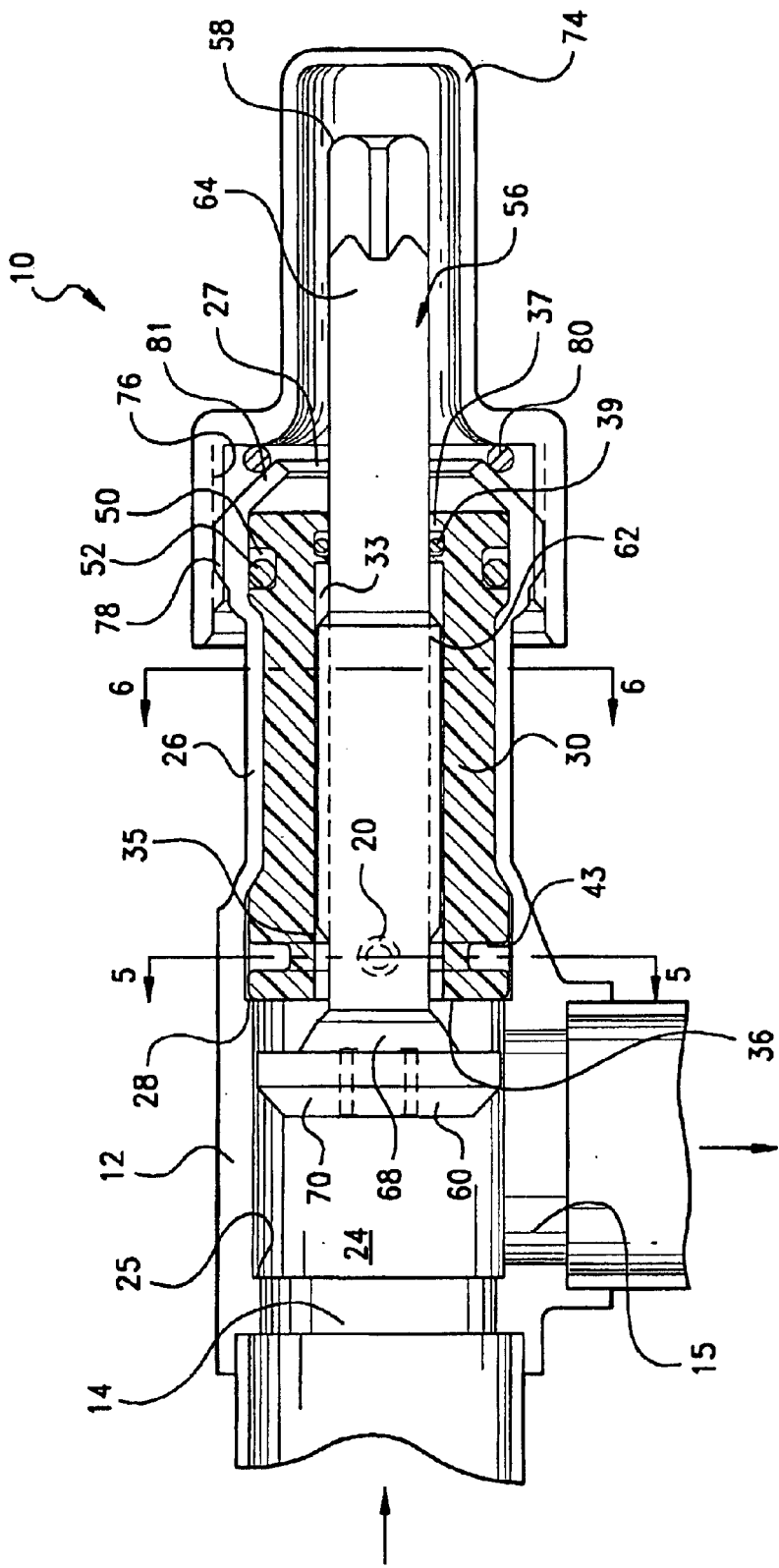
FIG. 4 is an enlarged view of a portion of the valve shown in FIG. 3.

The valve body includes a unitary piston plug retaining portion, indicated generally at 26, which projects outwardly from one end of the body, in an opposite axial direction from the first opening 14, to an open end 27. Body portion 26 preferably has a generally cylindrical configuration when the valve body is initially manufactured, and has a pliability which enables the portion 26 to be mechanically formed (e.g., crimped, coined or magnetically formed), yet is rigid enough to retain its shape over prolonged use. As shown in FIG. 4, an annular shoulder 28 is provided internally of body portion 26, and projects radially inward toward the central axis of the valve body, upstream from the service port 20. The reason for shoulder 28 will be explained in more detail below.

Finally, valve body 12 can include an integral flange or embossment as at 29 to enable the body to be secured at an appropriate location in the fluid system.

Valve body 12, including body portion 26, is preferably formed of a light weight-metal (e.g., brass) using conventional techniques (e.g., molding, shaping, stamping), although it could also be formed of plastics or elastomers (or other appropriate materials) in certain applications.

Figure 6:
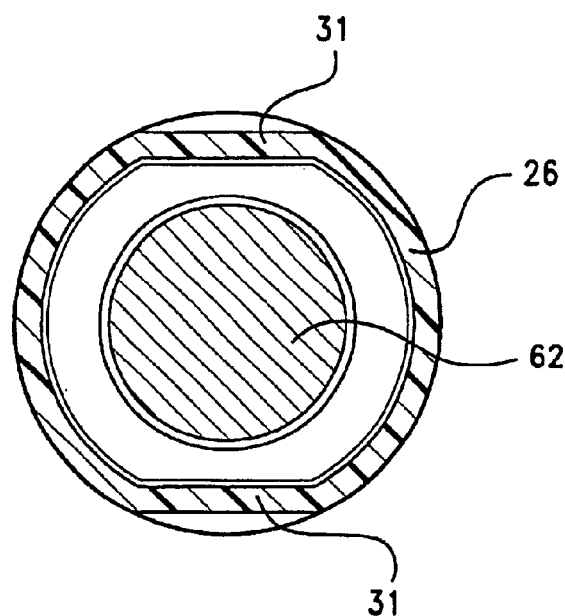
FIG. 6 is a cross-sectional end view of the valve taken substantially along the plane described by the lines 6—6 in FIG. 4.

Valve 10 further includes a valve plug, indicated generally at 30, closely received, preferably with a slip-fit, within valve body 12. Valve plug 30 has an elongated, generally cylindrical configuration, although the exterior surface along at least a portion of the valve plug preferably has a non-cylindrical geometry. As shown in FIG. 6, flats 31 are provided on opposite sides of the plug. A pair of flats are preferred, but the valve plug could have other external geometries, as will be explained further below.

Valve plug 30 further includes a central threaded through-bore 33, extending from one axial end of the plug to the other. The through-bore further includes a radially-enlarged counterbore portion 35 at the upstream end of the plug. A back or first circular valve seat 36 is defined at the upstream end of the plug, bounding the upstream end of counterbore 35. An annular flange, indicated generally at 37, projects radially inward into the through-bore at the downstream end of the plug. The annular flange 37 includes a radially-inwardly opening channel (not numbered) that receives and retains an O-ring seal 39.

The valve plug further includes an annular channel 43, outwardly surrounding the plug towards the upstream end. Channel 43 is axially aligned with and in fluid communication with service port 20 in valve body 12. Channel 43 is also in fluid communication with counterbore 35, and to this end, at least one, and preferably a plurality of radial openings 47 are provided in plug 30 (see FIG. 5).

Finally, the valve plug 30 includes a radially-outwardly opening channel 50 at the downstream end. A second O-ring seal 52 is received and retained in channel 50.

Valve plug 30 can be formed of a material appropriate for the particular application. Typically, this is brass, however, the present invention contemplates that the plug could be formed of material which is lighter in weight and less expensive than brass, such as a plastic or elastomer.

The valve further includes a valve element, indicated generally at 56. Valve element 56 includes an elongated valve stem 58, and an integral valve head 60. Valve stem 58 has a radially-enlarged or wider threaded portion 62, which threadably cooperates with the threaded through-bore 33 in the valve plug 30, such that the valve element can be screwed into and out of the valve plug. The valve stem also includes a radially-reduced or narrower portion 64, which projects axially outward from the downstream end of the valve plug, and outwardly from the end of the valve body, and is thereby externally accessible. The distal end of the valve stem is formed with an appropriate geometry (e.g., square or hex) to enable a tool (e.g., a wrench) to rotate the valve stem within the valve plug.

The narrower portion 64 of the valve stem has a smooth cylindrical exterior surface, and is closely received within the annular flange 37 of the valve plug. O-ring seal 39 carried by the channel in the flange 37 provides a fluid seal between valve plug 30 and valve stem 58 when the stem is rotated.

The valve head 60 has a circular configuration, and includes an annular tapered portion 68 on its back (downstream) surface, which sealingly engages the back valve seat 36 when the valve element is rotated in one direction into an open position. The valve head 60 also has an annular tapered portion 70 on its front (upstream) surface, which sealingly engages the front valve seat 25 when the valve element is rotated in an opposite direction into a closed position.

The valve stem and valve head are preferably formed unitary with each other, although it is possible that they could be formed of separate pieces, and later secured together. In any case, the valve element is preferably also formed of a material appropriate for the particular application, such as steel, although again, the valve stem could be formed of less-expensive and lighter weight material than steel, such as a plastic or elastomer.

As indicated above, the valve stem 64 extends outwardly from the end of the valve body and can be rotated to screw the valve element into or out of the valve plug. When the valve element is not being so rotated, a cup-shaped cap 74 can be secured to valve body 12 to protect the valve stem and valve plug from external elements. To this end, the cap can include a threaded portion 76, and the valve body 12 can include a corresponding threaded portion 78, which enable the cap to be easily screwed onto and off of the valve body. Of course, other techniques for securing the cap to the valve body, such as press-fit, could also be used. The cap can also carry an O-ring seal or packing 80, to provide a seal between the cap and the valve body. Cap 74 can also be formed of a material appropriate for the particular application, such as a metal, plastic or elastomer.

The present invention also contemplates a unique method for assembling the valve, which reduces assembling time and effort. To this end, the valve element 56 and valve plug 30 are initially pre-assembled by screwing the element into the plug. The tolerances and other functional and operating characteristics of the element and plug (such as the sealing engagement between the valve head 60 and the valve seat 36) can then be easily tested before being assembled with body 12. The O-rings 39 and 52 are then located on the valve plug, and the subassembly can then be inserted through the open end 27 of the valve body. The valve plug is inserted axially into the valve body from the open end 27, valve seat and valve head first, until the upstream end of the plug engages the shoulder 28 in the valve body. This axially locates the subassembly correctly in the body, and ensures that the channel 43 in the plug is in fluid communication with the service port 20. The rotational alignment of the valve plug within the valve body is not important as the annular channel 43 fluidly interconnects the service port 20 with radial opening(s) 47 in valve plug 30 regardless of its rotational orientation.

The valve plug is then fixedly retained within the valve body. While this can be done in a number of ways (e.g., welding, brazing, screw-fit), it is preferred that the valve body 12 is mechanically deformed to capture the valve plug. This reduces the braze/weld joints necessary for the valve, and allows less-expensive and lighter weight components to be used. It is preferred that the mechanical forming be accomplished by means such as crimping, coining or magnetic forming the valve body, such that the valve body adopts the exterior configuration of the valve plug. As mentioned above, the valve plug has a certain exterior geometry, and when the valve body is mechanically deformed around the valve plug to adopt the geometry, the geometry of the valve plug prevents the valve plug from rotating with respect to the valve body. As mentioned previously, this geometry could be a pair of flats on the valve plug, but it should be apparent that other geometries (such as a single flat, multiple flats, ribs, recesses, etc.) would suffice such that the valve body is essentially locked to the valve plug. Also as indicated above, other means for securing the valve plug and the valve body, such as staking, are also contemplated. In any case, it should be appreciated that after the mechanical forming, it is not possible to remove the valve plug and valve element from the valve body (that is, of course, not without substantial damage to the valve). This prevent disassembly of the valve in the field, and incorrect re-assembly, which could lead to leaks and spills, and inoperability of the valve.

To further facilitate preventing the valve plug from moving within the valve body, the downstream end of the valve body can also be narrowed or tapered down, as at 81, to the open end 27. Such narrowing can be accomplished by coining or by other conventional forming means. This in effect, traps the plug between the shoulder 28 and the narrowed down portion to prevent axial movement of the valve plug within the valve body. Thus, the mechanical forming of the valve body securely fixes the valve plug to the valve body and prevents relative movement therebetween.

After assembly of the valve and the connection of the valve within a fluid system, the valve can be used in open, closed or intermediate positions. The valve is useful for normal system operation where the valve element 56 is secured into an open position where the valve head 60 is in sealing engagement with the back valve seat 36 and fluid can flow substantially uninterrupted (without significant pressure drop) from the inlet passage 14 to the outlet passage 15. The valve element 56 can also be moved into a closed position, where the valve head 60 is in sealing engagement with the front valve seat 25, to prevent fluid flow through the valve during maintenance and shipping. The valve element can still further be moved into an intermediate position (illustrated in FIG. 4), where the valve head 60 is spaced from both the front and back valve seats, such that a flow path is opened to the service passage. The flow path can be used for evacuating, charging, reclaiming and pressure tapping the system. The stem cap 74 fits over the end of the valve body to enclose the stem when the valve element is not being rotated.

Thus, as described above, the present invention provides a back seating valve that has few braze/welding joints and few components, which reduces manufacturing and assembly costs, and reduces leak paths; and cannot be disassembled in the field.

What is claimed is:

1. A fluid control valve, comprising:
    a valve body having first, second and third fluid passages, the first and second fluid passages being fluidly interconnected, the valve body having a pliable retaining portion;
    a valve plug fixedly retained against rotation within the valve body by mechanical deformation of the retaining portion of the valve body into engagement with the valve plug, the valve plug including a back valve seat;
    a valve element including a stem and a valve head, the stem being received within a central bore in the valve plug and moveable to bring the valve head into and out of engagement with the back valve seat to close or open a flow path to the third fluid passage.

2. The fluid control valve as in claim 1, wherein the valve plug has an external non-cylindrical geometry, and the valve body has essentially the same external non-cylindrical geometry after deformation, the geometry of the valve plug and valve body cooperating to prevent the valve plug from rotating within the valve body.

3. The fluid control valve as in claim 1, wherein an end portion of the valve stem projects externally from the valve body and can be accessed to move the valve element between the open and closed positions.

4. The fluid control valve as in claim 1, wherein both the valve plug and the valve stem have corresponding threads that enable the valve element to be screwed into and out of the valve plug to bring the valve head into and out of sealing engagement with the back valve seat.

5. The fluid control valve as in claim 1, wherein the valve plug includes an annular channel outwardly surrounding the plug and in fluid connection with the third fluid passage in the valve body, the channel also fluidly connected with the first and second fluid passages when the flow path is open.

6. The fluid control valve as in claim 5, wherein the valve plug includes a radial opening fluidly interconnecting the annular channel with the central bore of the valve plug.

7. The fluid control valve as in claim 6, wherein the central bore in the valve plug includes a radially enlarged counterbore portion opening at an upstream end of the valve plug to receive fluid when the valve head is out of engagement with the valve seat, and the radial opening is fluidly interconnected with the enlarged portion of the central bore.

8. The fluid control valve as in claim 1, wherein an O-ring seal is provided between the valve stem and the valve plug to provide a fluid-tight seal therebetween.

9. The fluid control valve as in claim 1, wherein the back valve seat is defined at an upstream end of the valve plug.

10. The fluid control valve as in claim 1, wherein the valve body includes an internal, radially-projecting annular shoulder, said shoulder axially locating the valve plug in the valve body.

11. The fluid control valve as in claim 10, wherein the valve body narrows at a downstream end, such that the valve plug is captured between the annular shoulder and the narrow portion of the valve body.

12. The fluid control valve as in claim 1, and further including a front valve seat defined in the valve body, axially opposite from the back valve seat, and the valve element is further movable to bring the valve head into and out of engagement with the front valve seat to allow or prevent fluid flow between the first fluid passage and the second fluid passage.

13. The fluid control valve as in claim 1, wherein the pliable retaining portion is intermediate upstream and downstream ends of the valve body.

14. The fluid control valve as in claim 13, wherein the valve plug includes radially enlarged upstream and downstream ends, and a radially narrower central portion, the retaining portion of the valve body corresponding to the narrow central portion of the valve plug, and having a reduced diameter as compared to the portions of the valve body at the upstream and downstream ends.

15. The fluid control valve as in claim 14, wherein the valve body includes an internal, radially-projecting annular shoulder, said shoulder axially locating the valve plug in the valve body, and the valve body narrows at the downstream end, downstream of the enlarged downstream end of the valve plug, such that the valve plug is captured between the annular shoulder and the narrow downstream end portion of the valve body, to prevent axial movement of the valve plug relative to the valve body.

16. The fluid control valve as in claim 15, wherein the plug has one or more external flats, and the valve body conforms to the flats to prevent the valve plug from rotating within the valve body.

17. A back-seating valve, comprising:
    a valve body having an inlet passage and an outlet passage which are fluidly interconnected, and a service passage, the valve body including a pliable annular valve plug retaining portion projecting outwardly from one end of the valve body;
    an annular valve plug located in the valve plug retaining portion of the valve body and fixedly retained therein by mechanical deformation of the valve plug retaining portion cooperating with the valve plug to prevent the valve plus from rotating within the valve body, the valve plug including a threaded through-bore, and an upstream end defining an annular back valve seat bounding the upstream end of the through-bore;
    a valve element including an elongated stem and an integral, enlarged valve head, the stem being threadably received within the threaded through-bore in the piston plug and including an end portion projecting outwardly from a downstream end of the valve body and externally accessible and rotatable in one direction to bring the valve head into sealing engagement with the back valve seat to prevent flow from the inlet and outlet passages to the service port, and rotatable in another direction to bring the valve head out of sealing engagement with the back valve seat to open a flow path from the inlet and outlet passage to the service port.

18. The back-seating valve as in claim 17, wherein the valve plug has an external non-cylindrical geometry, and the valve body has essentially the same external non-cylindrical geometry after deformation, the geometry of the valve plug and valve body cooperating to fix the valve plug with respect to the valve body and prevent the valve plug from rotating within the valve body.

19. The back-seating valve as in claim 17, wherein the valve plug includes an annular channel outwardly surrounding the plug and in fluid connection with the service passage in the valve body, the channel also in fluid connection with the inlet passage when the valve head is out of sealing engagement with the valve plug.

20. The fluid control valve as in claim 19, wherein the valve plug includes a plurality of radial openings fluidly interconnecting the annular channel through the central bore in the valve plug.

21. The back-seating valve as in claim 20, wherein the through-bore in the valve plug includes a radially enlarged counterbore portion opening at the valve seat to receive fluid when the valve head is out of engagement with the valve seat, the radial openings fluidly interconnected with the enlarged portion of the through-bore.

22. A The back-seating valve as in claim 17, wherein an O-ring seal is provided between the valve stem and the valve plug to provide a fluid-tight seal there-between.

23. The back-seating valve as in claim 17, wherein an O-ring seal is provided between the valve plug and the valve body to provide a fluid-tight seal therebetween.

24. The back-seating valve as in claim 17, wherein the valve body includes an internal, radially-projecting annular shoulder, said shoulder axially locating the valve plug in the valve body.

25. The back-seating valve as in claim 24, wherein the valve body narrows at a downstream end, such that the valve plug is captured between the annular shoulder and the narrow portion of the valve body.

26. The back-seating valve as in claim 17 and further including a front valve seat in the valve body, axially opposite from the back valve seat, and the valve element is further moveable to bring the valve head into and out of engagement with the front valve to allow or prevent fluid flow between the inlet passage and the outlet passage.

27. The back-seating valve as in claim 17, wherein the pliable retaining portion is intermediate upstream and downstream ends of the valve body.

28. The back-seating valve as in claim 27, wherein the valve body radially enlarged upstream and downstream ends, and a radially narrower central portion, the retaining portion of the valve body corresponding to the narrow central portion of the valve plug, and having a reduced diameter as compared to the portions of the valve body at the upstream and downstream ends.

29. The back-seating valve as in claim 28, wherein the valve body includes an internal, radially-projecting annular shoulder, said shoulder axially locating the valve plug in the valve body, and the valve body narrows at the downstream end, downstream of the enlarged downstream end of the valve plug, such that the valve plug is captured between the annular shoulder and the narrow downstream end portion of the valve body, to prevent axial movement of the valve plug relative to the valve body.

30. The back-seating valve as in claim 29, wherein the plug has one or more external flats, and the valve body conforms to the flats to prevent the valve plug from rotating within the valve body.

31. A back-seating valve, comprising:
a valve body having an inlet passage and an outlet passage which are fluidly interconnected, and a service passage, a front valve seat defined in the valve body at the inlet passage, the valve body including a pliable annular valve plug retaining portion projecting outwardly from one end of the valve body;
an annular valve plug located in the valve plug retaining portion of the valve body and fixedly retained therein by mechanical deformation of the valve body into engagement with a non-cylindrical portion of the valve plug to prevent rotation of the valve plug within the valve body the valve plug including an upstream end defining a back valve seat;
a valve element including an elongated stem and an integral, enlarged valve head, the stem being threadably received within a threaded through-bore in the valve plug and including an end portion projecting outwardly from a downstream end of the valve body and externally accessible and rotatable in one direction into a closed position to bring the valve head into sealing engagement with the back valve seat to close a flow path to the service port, and rotatable in another direction into an intermediate position to bring the valve head out of sealing engagement with the back valve seat to open the flow path to the service port, and further rotatable in the other direction into a closed position to bring the valve head into sealing engagement with the front valve seat to prevent fluid flow between the inlet and outlet passages, wherein the valve plug includes an annular channel outwardly surrounding the plug and fluidly connected with the service passage in the valve body, the channel also fluidly connected with the inlet and outlet passage when the valve head is in the intermediate position.

32. The fluid control valve as in claim 31, wherein the valve plug includes a series of radial openings fluidly interconnecting the annular channel with the threaded through-bore.

33. The back-seating valve as in claim 32, wherein the central through-bore in the valve plug includes a radially enlarged counterbore portion opening at the valve seat to receive fluid when the valve head is out of engagement with the valve seat, and the radial openings fluidly interconnect the annular channel with the enlarged counterbore portion of the through-bore.

34. The back-seating valve as in claim 31, wherein the valve body is mechanically deformed to prevent movement of the valve plug with respect to the valve body.

35. The back-seating valve as in claim 31, wherein the pliable retaining portion is intermediate upstream and downstream ends of the valve body.

36. The back-seating valve as in claim 35, wherein the valve plug includes radially enlarged upstream and downstream ends, and a radially narrower central portion, the retaining portion of the valve body corresponding to the narrow central portion of the valve plug, and having a reduced diameter as compared to the portions of the valve body at the upstream and downstream ends.

37. The back-seating valve as in claim 36, wherein the plug has one or more external flats, and the valve body conforms to the flats to prevent the valve plug from rotating within the valve body.

38. The back-seating valve as in claim 37, wherein the plug has one or more external flats, and the valve body conforms to the flats to prevent the valve plug from rotating within the valve body.

39. A back-seating valve, comprising:
a valve body having an inlet passage and an outlet passage which are fluidly interconnected, and a service passage, a front valve seat defined in the valve body at the inlet passage, the valve body including a pliable annular valve plug retaining portion projecting outwardly from one end of the valve body;
an annular valve plug located in the valve plug retaining portion of the valve body and fixedly retained therein by mechanical deformation of the valve plug retaining portion cooperating with a non-cylindrical portion of the valve body to prevent relative rotation thereof, the valve plug including a threaded through-bore, and an upstream end defining an annular back valve seat bounding the upstream end of the through-bore;
a valve element including an elongated stem and a valve head, the stem being threadably received within the threaded through-bore in the valve plug and including an end portion projecting outwardly from a downstream end of the valve body and externally accessible and rotatable in one direction into a closed position to bring the valve head into sealing engagement with the back valve seat to close a flow path to the service port, and rotatable in another direction into an intermediate position to bring the valve head out of sealing engagement with the back valve seat to open the flow path to the service port, and further rotatable in the other direction into a closed position to bring the valve head into sealing engagement with the front valve seat to prevent fluid flow between the inlet and the outlet passages, the valve plug including an annular channel outwardly surrounding the plug and fluidly connected with the service passage in the valve body, the channel also fluidly connected with the inlet and outlet passages when the valve head is in the intermediate position.

40. The back-seating valve as in claim 39, wherein the pliable retaining portion is intermediate upstream and downstream ends of the valve body.

41. The back-seating valve as in claim 40, wherein the valve plug includes radially enlarged upstream and downstream ends, and a radially narrower central portion, the retaining portion of the valve body corresponding to the narrow central portion of the valve plug, and having a reduced diameter as compared to the portions of the valve body at the upstream and downstream end.

42. The back-seating valve as in claim 41, wherein the valve body includes an internal, radially-projecting annular shoulder, said shoulder axially locating the valve plug in the valve body, and the valve body narrows at the downstream end, downstream of the enlarged downstream end of the valve plug, such that the valve plug is captured between the annular shoulder and the narrow downstream end portion of the valve body, to prevent axial movement of the valve plug relative to the valve body.

43. The back-seating valve as in claim 42, wherein the plug has one or more external flats, and the valve body conforms to the flats to prevent the valve plug from rotating within the valve body.

* * * * *